(12) United States Patent
Farazi et al.

(10) Patent No.: US 8,032,206 B1
(45) Date of Patent: Oct. 4, 2011

(54) USE OF MOTION SENSOR FOR DYNAMIC UPDATING OF HEART DETECTION THRESHOLD

(75) Inventors: Taraneh Ghaffari Farazi, San Jose, CA (US); Yelena Nabutovsky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 998 days.

(21) Appl. No.: 11/255,906

(22) Filed: Oct. 20, 2005

(51) Int. Cl.
*A61B 5/024* (2006.01)
(52) U.S. Cl. .......................... 600/509; 600/521; 600/536
(58) Field of Classification Search .................. 600/509, 600/536, 521; 607/4, 2, 28
See application file for complete search history.

(56) References Cited

U.S. PATENT DOCUMENTS

| | | | |
|---|---|---|---|
| 5,178,151 A * | 1/1993 | Sackner | 600/526 |
| 5,273,036 A * | 12/1993 | Kronberg et al. | 600/310 |
| 5,738,104 A * | 4/1998 | Lo et al. | 600/521 |
| 6,230,059 B1 * | 5/2001 | Duffin | 607/60 |
| 6,415,174 B1 * | 7/2002 | Bebehani et al. | 600/513 |
| 6,449,509 B1 * | 9/2002 | Park et al. | 607/20 |
| 6,480,111 B2 | 11/2002 | Canady et al. | 340/573.1 |
| 6,491,647 B1 * | 12/2002 | Bridger et al. | 600/500 |
| 6,675,036 B2 * | 1/2004 | Kreger et al. | 600/413 |
| 7,336,997 B2 * | 2/2008 | Fukui | 607/17 |
| 2001/0026222 A1 | 10/2001 | Canady, Jr. et al. | 340/573.1 |
| 2004/0186388 A1 * | 9/2004 | Gerasimov | 600/519 |
| 2005/0251056 A1 * | 11/2005 | Gribkov et al. | 600/509 |

* cited by examiner

*Primary Examiner* — Scott Getzow
*Assistant Examiner* — Joseph Dietrich
(74) *Attorney, Agent, or Firm* — Steven M. Mitchell

(57) ABSTRACT

A method for accurate heart rate detection includes receiving a signal indicative of motion due to respiration, and using the signal indicative of motion to adjust a threshold value of a signal indicative of activity of the heart. The adjusted threshold value is used to detect an accurate heart rate of a patient. A system for accurate heart rate detection comprises a motion sensor which produces a signal indicative of motion due to respiration, and a processor which adjusts a threshold value of a signal indicative of activity of the heart according to the signal indicative of motion. The adjusted threshold value is used to detect an accurate heart rate of a patient. The motion sensor can be any device that can determine direction of motion, such as an accelerometer, a displacement sensor, a velocity sensor, or a photoplethysmography (PPG) sensor.

28 Claims, 9 Drawing Sheets

USE OF MOTION SENSOR FOR DYNAMIC UPDATING OF HEART DETECTION THRESHOLD

BACKGROUND OF THE INVENTION

1. Field of the Invention

The present invention relates generally to heart rate detection. More particularly, the invention relates to improving heart rate detection accuracy by reducing the influence of physical activity.

2. Background of the Invention

An electrocardiogram (ECG) is a measurement of the electrical signals given off by the beating of the heart. The R waves, which are the noticeable upward spikes on an ECG trace, occur during contraction of the heart and are part of the QRS complex. Thresholding is one method of determining a patient's heart rate, and involves detecting when the R wave amplitude exceeds a predetermined threshold value. However, the real time detection of heart rates is challenging in the presence of amplitude fluctuations that are due to motion.

An example of such a scenario is the detection of R-waves measured either from surface or subcutaneous electrodes placed in the chest area. Respiration induced motion artifact is especially problematic when a patient's breathing is being controlled by a respirator. In this case, exaggerated inflation and deflation of the lungs causes the rise and fall of the chest cavity at a frequency several times lower than the cardiac rate. This rise and fall can cause amplitude fluctuations in the signal measured from the electrodes.

An increase in amplitude can cause detection of portions of the ECG other than the R wave, resulting in spurious beat detections. Conversely, a decrease in amplitude can cause missed detection of R waves, resulting in missed beat detections. Thus, amplitude fluctuations may result in an inaccurate heart rate determination.

Another example is the subcutaneous photoplethysmography (sPPG) sensor, which is extremely sensitive to motion. The real time PPG signal fluctuates greatly with respiration due to motion artifact as well as change in venous blood volume that accompanies each breath.

High-pass filters have been used to remove low-frequency components from the cardiac signal. However, such an approach requires the added complexity of a filter to obtain an accurate heart rate.

What is needed is a more efficient way to detect heart rate in the presence of physical motion such as that due to respiration.

BRIEF SUMMARY OF THE INVENTION

The present invention includes a method and system for accurate heart rate detection. The method includes the steps of receiving a signal indicative of motion due to respiration, and using the signal indicative of motion to adjust a threshold value of a signal indicative of activity of the heart. The adjusted threshold value is used to detect an accurate heart rate of a patient.

The system includes a motion sensor which produces a signal indicative of motion due to respiration, and a processor which adjusts a threshold value of a signal indicative of heart rate according to the signal indicative of motion. The adjusted threshold value is used to detect an accurate heart rate of a patient. The motion sensor can be any device that can determine direction of motion, such as an accelerometer, a displacement sensor, or a velocity sensor.

Further features and advantages of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements, and the drawing in which an element first appears is typically indicated by the leftmost digit(s) in the corresponding reference number.

DETAILED DESCRIPTION OF THE INVENTION

Overview

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

It is noted that references in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described.

Description of Thresholding Detection and the Effect of Respiration

The easiest method of pulse detection is thresholding, which involves finding the time when the signal becomes greater than a given value and then finding the maximum value in a window following the time of the threshold crossing. Each detected peak is followed by a refractory period during which no detections can be made.

Figure 1:
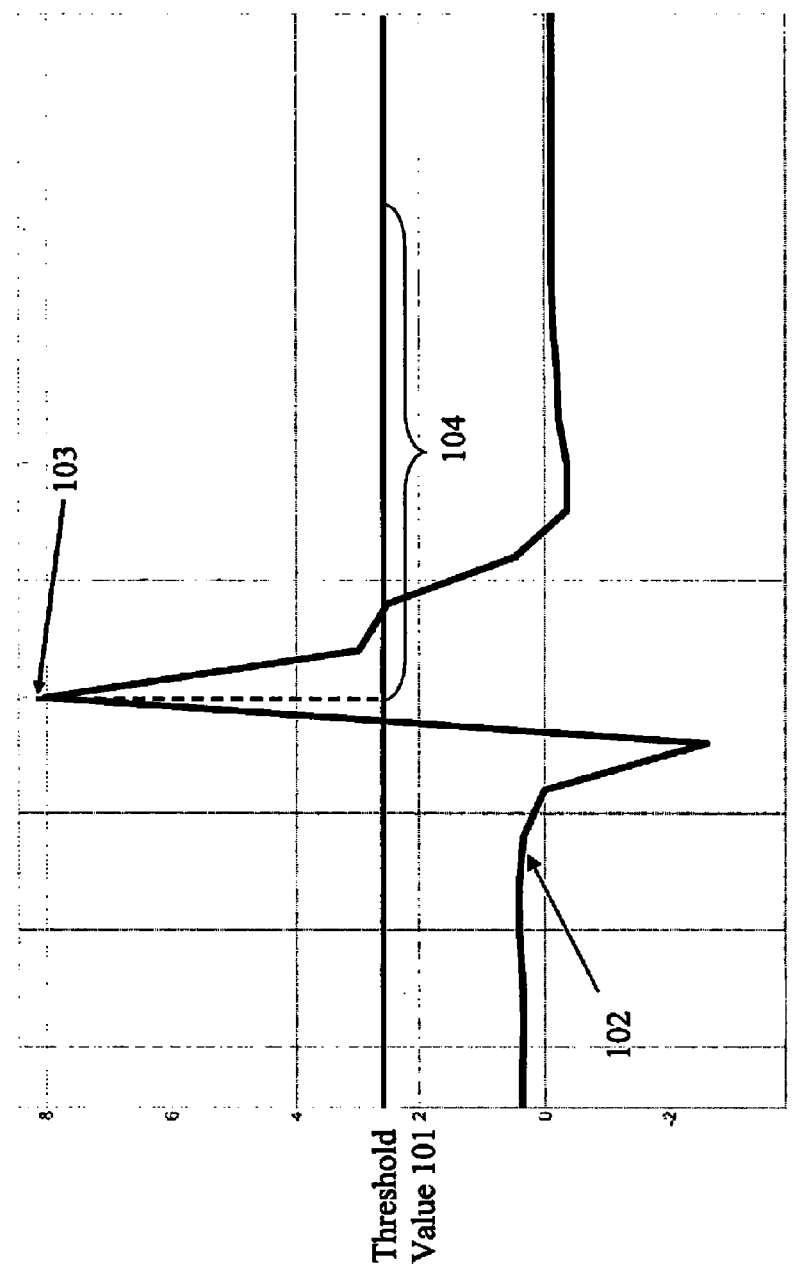
FIG. 1 is a representative electrocardiogram (ECG) signal illustrating heart rate detection using a threshold value.

FIG. 1 is a representative electrocardiogram (ECG) signal illustrating heart rate detection using a threshold value 101. Thresholding is a method of heart rate detection, which includes detecting the time at which a representative cardiac signal 102 becomes greater than the threshold value 101. Once representative cardiac signal 102 becomes greater than threshold value 101, a maximum value 103 of representative cardiac signal 102 following the threshold crossing can be detected. Maximum value 103 usually corresponds with the R-wave of the QRS complex, which is an electrical signal given off during contraction of the heart. Detection of maximum value 103 is usually followed by a refractory period 104 during which no detections can be made.

Respiratory waves often occur at a frequency several times lower than the cardiac rate. The lower-frequency respiratory wave causes amplitude fluctuations of the measured cardiac signal. Using the thresholding method to detect individual heart rates in the presence of heart rate amplitude fluctuations can be challenging, because amplitude fluctuations may result in inaccurate heart rate detection. This problem can arise during detection of cardiac signals in the presence of strong respiration. Particularly, when a subject is on a respirator the inflation and deflation of the lungs is exaggerated and rib cage movement can disturb measurements of the cardiac signal. Two examples of cardiac signal measurement are recordings from subcutaneous or surface electrodes placed on the chest and subcutaneous photoplethysmography (sPPG) sensor recordings. In both cases, the frequency of respiratory waves is considerably lower than that of cardiac pulses.

Figure 2:
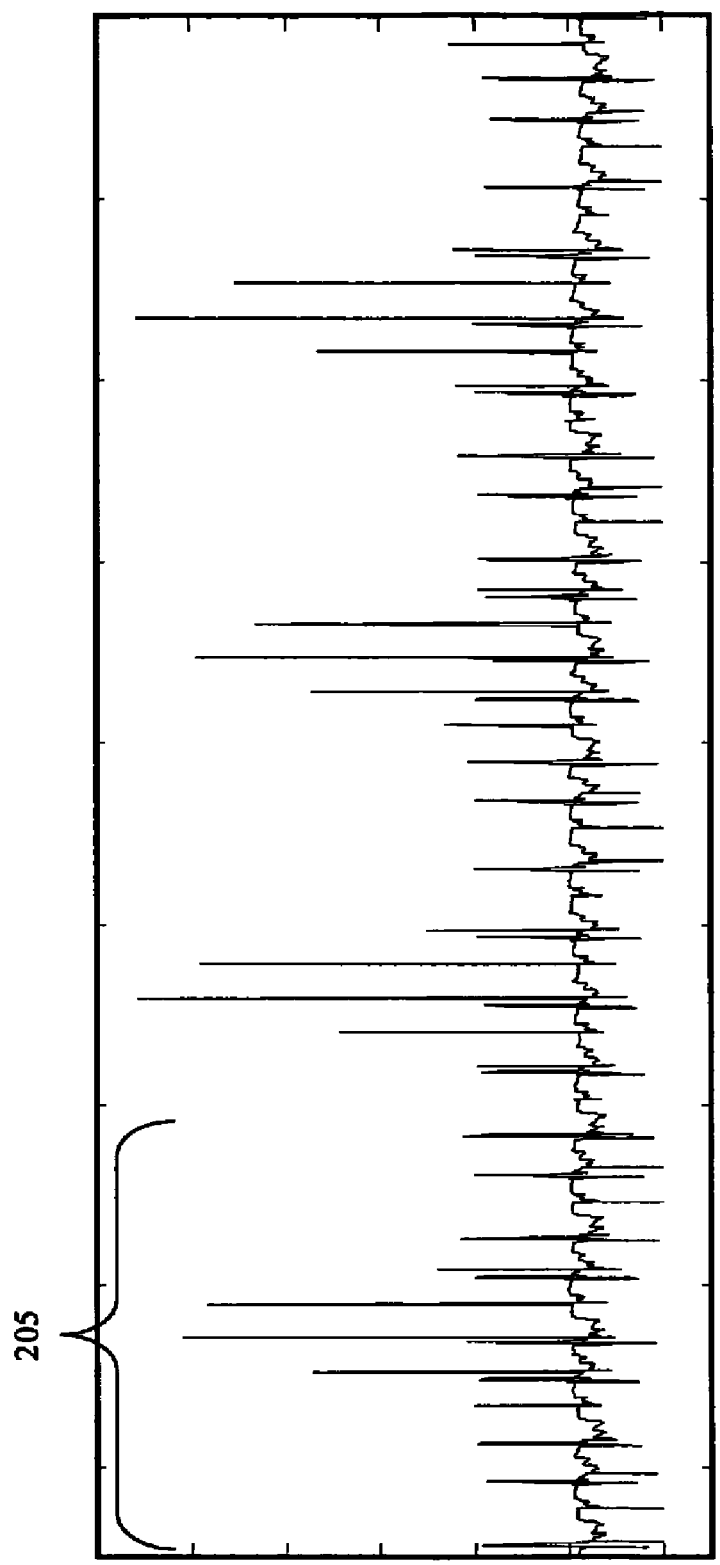
FIG. 2 is an example electrocardiogram (ECG) trace illustrating amplitude fluctuations due to respiration motion in a canine.

An example of the effect of respiration on a cardiac signal is illustrated in FIG. 2. FIG. 2 is an electrocardiogram (ECG) trace being recorded from subcutaneous electrodes on the chest of a canine, while the animal is being paced in the right ventricle at a rate of 160 beats per minute. As shown in bracketed portion 205 of the recording, the amplitude of the R-waves changes dramatically with respiration.

Figure 3A:
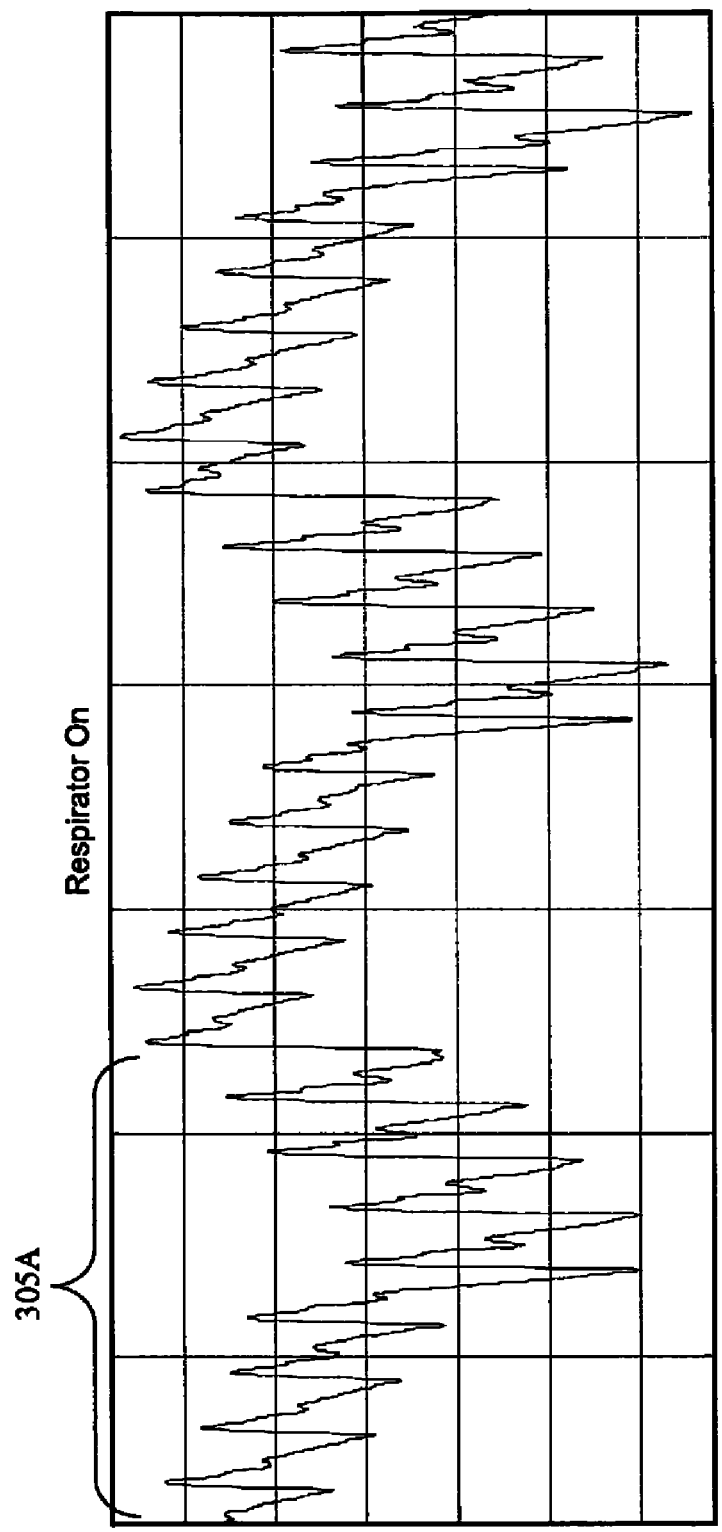
FIGS. 3A-3B are example photoplethysmography (PPG) traces from a canine on and off a respirator, respectively, illustrating amplitude fluctuations due to respiration motion in a canine.
Figure 3B:
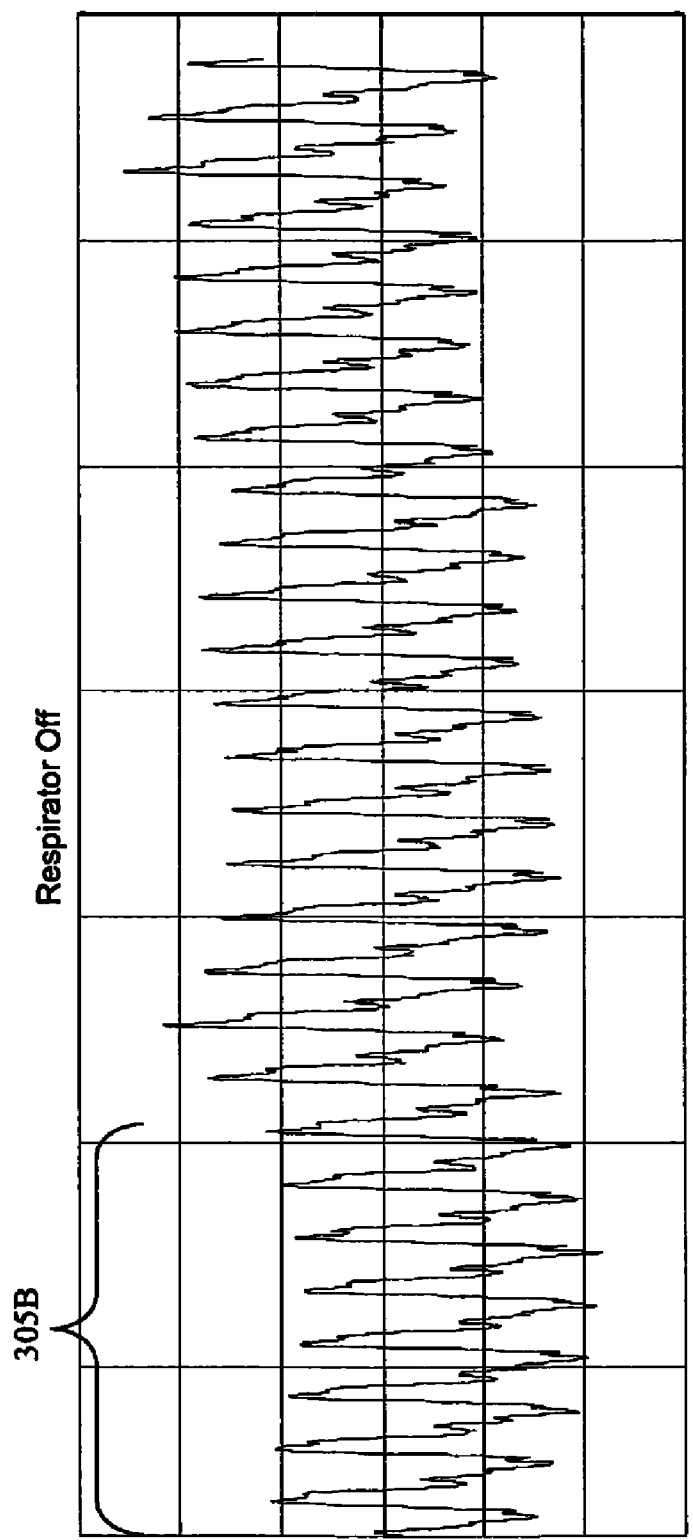

Another example of the effect of respiration on a cardiac signal is illustrated in FIGS. 3A-3B. FIGS. 3A-3B are subcutaneous photoplethysmography (sPPG) traces being recorded from a sensor placed in the dorsolateral thorax of a canine with the subject on and off a respirator. When the subject is on a respirator, the inflation and deflation of the lungs is exaggerated and rib cage movement can disturb measurements of the cardiac signal. In FIG. 3A, the respirator is turned on and large fluctuations due to respiration are visible in the recording at bracketed portion 305A. The large fluctuations of bracketed portion 305A are mostly due to the sPPG's high sensitivity to motion. With each breath, the rib cage moves and causes a shift in the baseline. In FIG. 3B, the respirator is turned off, and the large fluctuations are substantially reduced as visible in the recording at corresponding bracketed portion 305B. Since it is not possible to turn the respirator off for too long without significant potential of danger to the patient, this is not a viable option for dealing with the baseline fluctuations.

As illustrated in FIGS. 2, 3A and 3B, respiration motion causes significant fluctuations in the amplitude of both ECG and PPG signals. Thus, thresholding accuracy for both ECG and sPPG signals could be greatly improved if the effects of such amplitude fluctuations could be taken into account.

System for Dynamically Updating the Threshold Value

A system for ameliorating the above-described problems and for determining an accurate heart rate of a patient will be described. A motion sensor, such as an accelerometer, can be used to detect chest movement due to respiration and the output can be fed back to adjust the threshold of the ECG or sPPG reading. The motion sensor is typically placed on the exterior of the chest region of a patient. The patient will generally be supine at this time.

The motion sensor can either be part of an electrode or sensor module or can be placed next to the electrode or sensor module. In this case, it is sufficient to have the motion sensor operating in the y-axis only. As the subject is inhaling and exhaling, the motion sensor will respond to the movements of the chest. The motion sensor produces a signal indicative of physical motion (e.g., the rise and fall of the chest as a result of respiration). The motion signal is provided as an input to an ECG machine for use in adjusting a threshold value. For example, in the case of an ECG signal, the motion signal can be used to adjust threshold value 101 (see FIG. 1). The motion sensor signal can also be used to adjust a threshold value used with a physiologic signal sensed by other sensors (e.g., a signal from a strain gauge or PPG sensor representing blood volume).

The motion sensor measures a parameter indicative of motion (e.g., due to respiration) and converts the measured parameter to a motion signal. The motion sensor can be any device capable of determining the direction of detected motion, such as an accelerometer, a displacement sensor, or a velocity sensor. For example, if the motion sensor is a displacement sensor which measures the actual displacement of the chest, the threshold value 101 would be a function of the amount of displacement.

Figure 8:
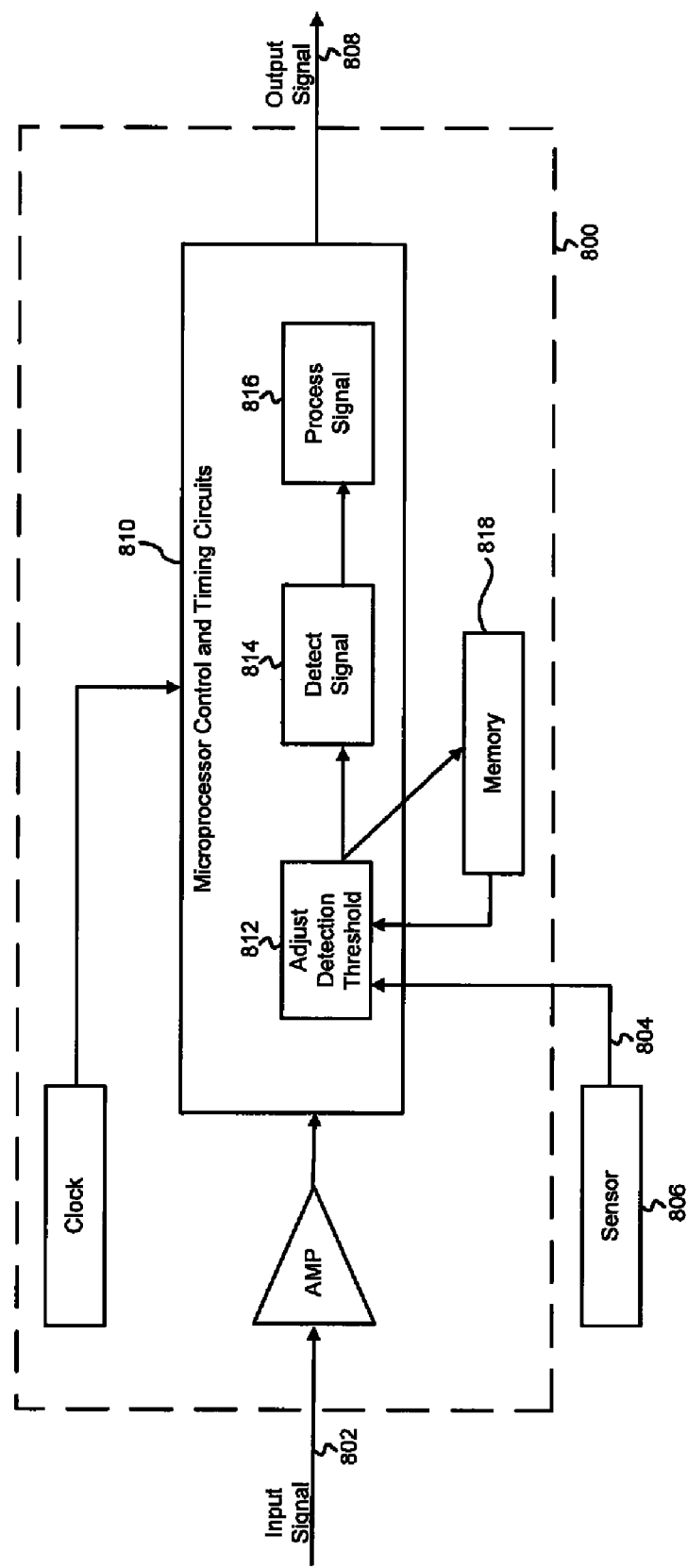
FIG. 8 shows a system for use in dynamically updating the heart rate detection threshold.

FIG. 8 shows an embodiment of a system for adjusting the cardiac detection threshold. A thresholding circuit 800 has an input 802 which receives an input ECG signal, an input 804 which carries an input signal from a motion sensor 806, and an output 808 which produces an output signal that represents an accurate detected heart rate of a patient. Thresholding circuit 800 also comprises a microcontroller 810. Microcontroller 810 comprises a threshold detection circuit 812, a signal detection circuit 814 and a signal processing circuit 816. Thresholding circuit 800 also includes a memory module 818. Memory module 818 stores the detection threshold.

In operation, surface or subcutaneous ECG detectors placed on or below the skin surface, usually in the region of the heart, as is well known to those skilled in the medical diagnostic field, produce a signal that is provided at input 802 to thresholding circuit 800. Alternatively, the output signal from an sPPG sensor provides input signal 802. At the same time, a motion sensor, such as an accelerometer, produces a signal indicative of movement of the chest, as with respiration. The motion sensor signal is provided though input 804 to threshold detection circuit 812. Threshold detection circuit 812 adjusts the detection threshold based on the input signal from sensor 806. The adjusted threshold is stored in memory 818 and replaces the initial and any previously stored threshold value.

Signal detection circuit 814 detects the ECG signal from input 802 based on the adjusted threshold from circuit 812.

The detected signal is processed in signal processor 816 and is output at output 808 to an appropriate display or other telemetry device.

Referring back to FIG. 1, microcontroller 810 adjusts threshold value 101 according to the motion signal 804. The adjusted threshold value 101 is used to detect an accurate heart rate of a patient. Alternatively stated, the motion signal is a parameter representing the motion of the chest that microcontroller 810 uses to dynamically update the threshold value 101.

Figure 4:
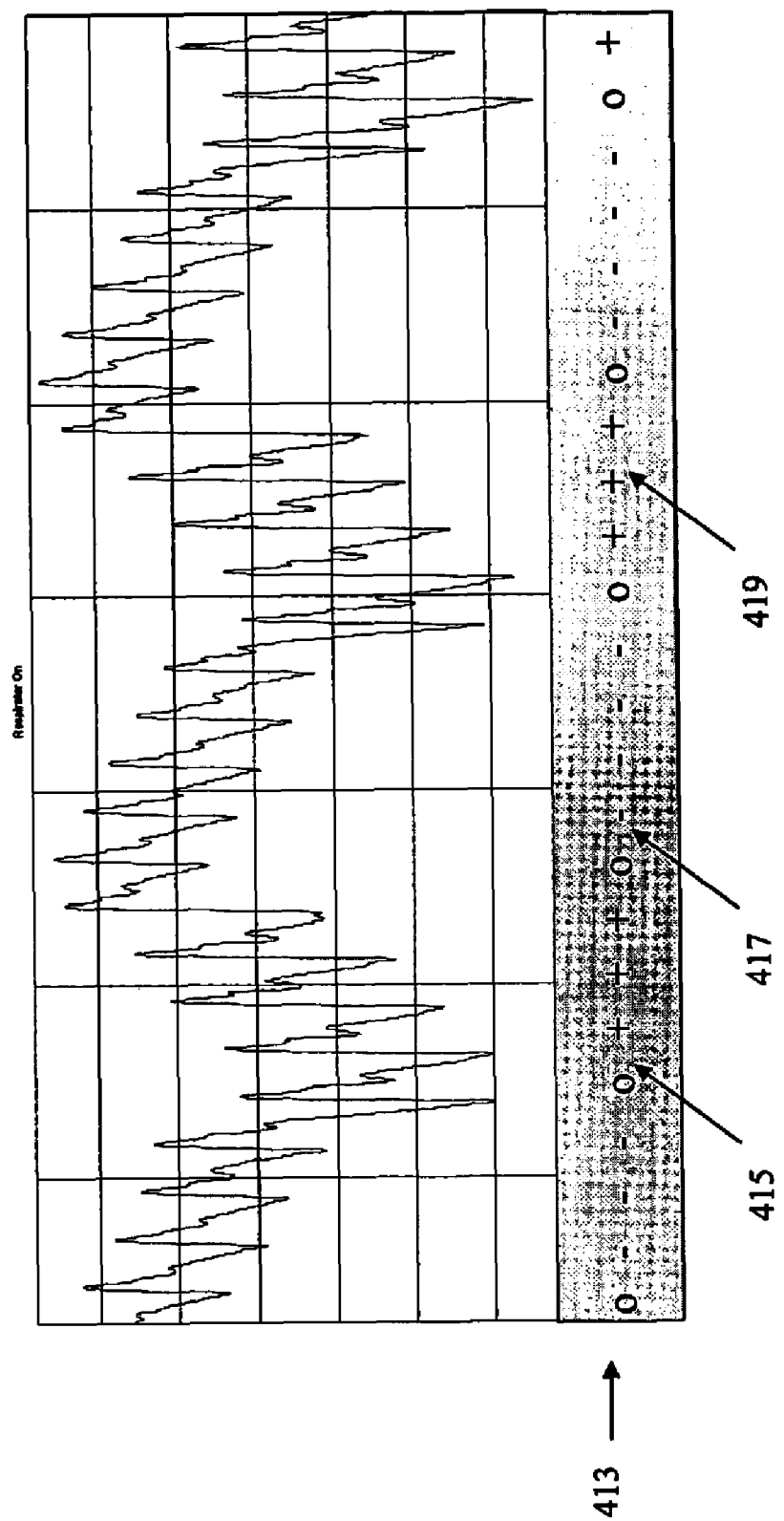
FIG. 4 is the example PPG trace of FIG. 3A with a corresponding motion sensor output.

FIG. 4 shows the PPG trace of FIG. 3A along with a simulated, corresponding motion sensor output 413 from, for example, an accelerometer. In this example, output 413 contains symbol 415 (e.g., "+") corresponding to upward movement of the chest, symbol 417 (e.g., "−") corresponding to downward movement of the chest, and symbol 419 (e.g., "o") corresponding to no movement of the chest.

Microcontroller 810 uses motion sensor output 413 (corresponding to sensor signal 804 in FIG. 8) to dynamically update the threshold value 101 in order to detect an accurate heart rate. Microcontroller 810 could also use motion sensor output 413 to dynamically update a threshold value to detect an accurate heart rate from the illustrated PPG signal. In either case, if motion sensor output 413 indicates an upward movement of the chest (such as symbol 415), the threshold value can be increased. If motion sensor output 413 indicates a downward movement of the chest (such as symbol 417), threshold value 101 can be decreased. If motion sensor output 413 indicates no significant movement of the chest (such as symbol 419), threshold value 101 can remain constant.

Method for Dynamically Updating the Threshold Value

Figure 5:
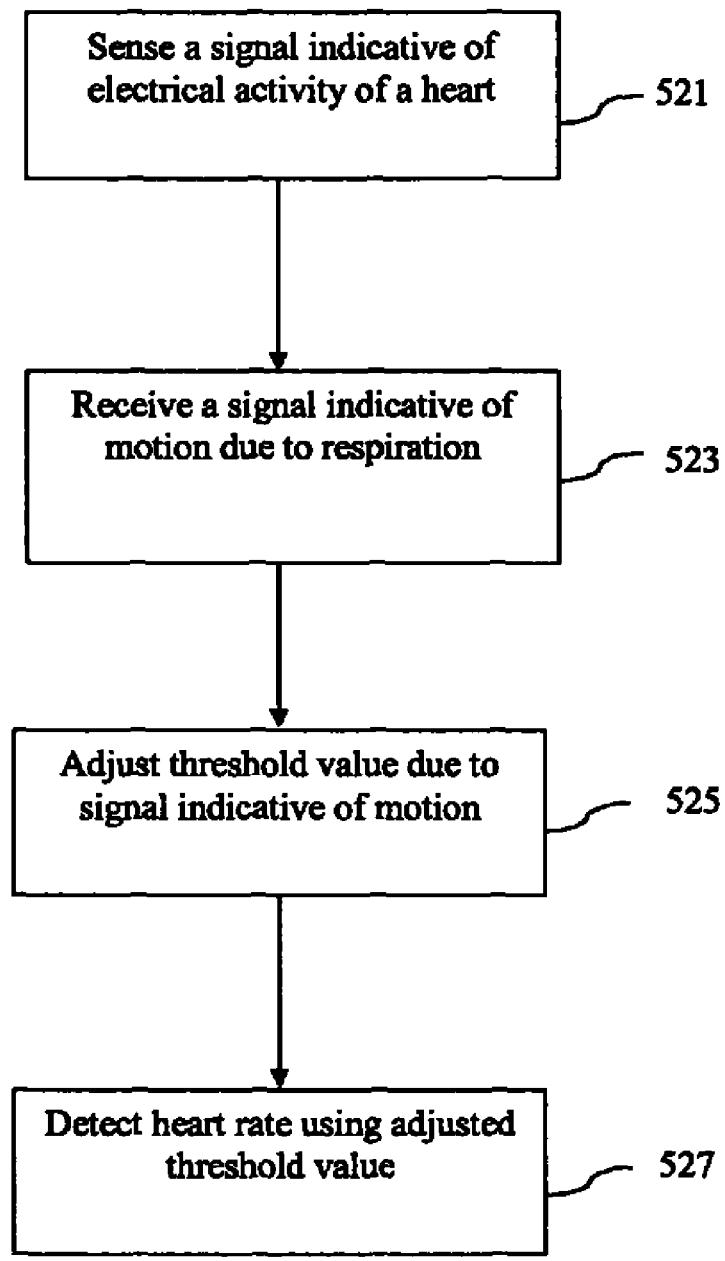
FIG. 5 shows a high-level process flowchart for detecting a heart rate.

FIG. 5 shows a high-level process flowchart for detecting a heart rate. The steps of FIG. 5 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described below in detail.

The process depicted in FIG. 5 for detecting a heart rate begins with step 521. In step 521, a signal indicative of electrical activity of a heart is sensed and received by a processor. Example signals indicative of electrical activity of a heart include an electrocardiogram (ECG) signal. Example devices for sensing a signal indicative of electrical activity of a heart include surface electrodes placed on a chest area, subcutaneous electrodes placed in a chest area, a PPG sensor representing blood volume, and any other sensors capable of measuring parameters indicative of the electrical activity and/or blood flow of the heart.

In step 523, a signal indicative of motion due to respiration is received by a processor. As discussed above, example devices for sensing a signal indicative of motion due to respiration include any device which can determine the direction of motion, such as an accelerometer, a displacement sensor, or a velocity sensor.

In step 525, the signal indicative of motion is used to adjust the threshold value for the signal indicative of electrical activity of the heart. If the signal indicative of motion indicates an upward movement of the chest, the threshold value will be increased. If the signal indicative of motion indicates a downward movement of the chest, the threshold value will be decreased. If the signal indicative of motion indicates no significant movement of the chest, the threshold value will remain constant.

In step 527, the adjusted threshold value is used to detect a heart rate of a patient. The threshold value is dynamically updated according to the signal indicative of motion due to respiration, and is used to ensure accurate pulse detection. Dynamic updating may involve continuous updating or periodic updating (e.g., 20 updates per second).

Figure 6:
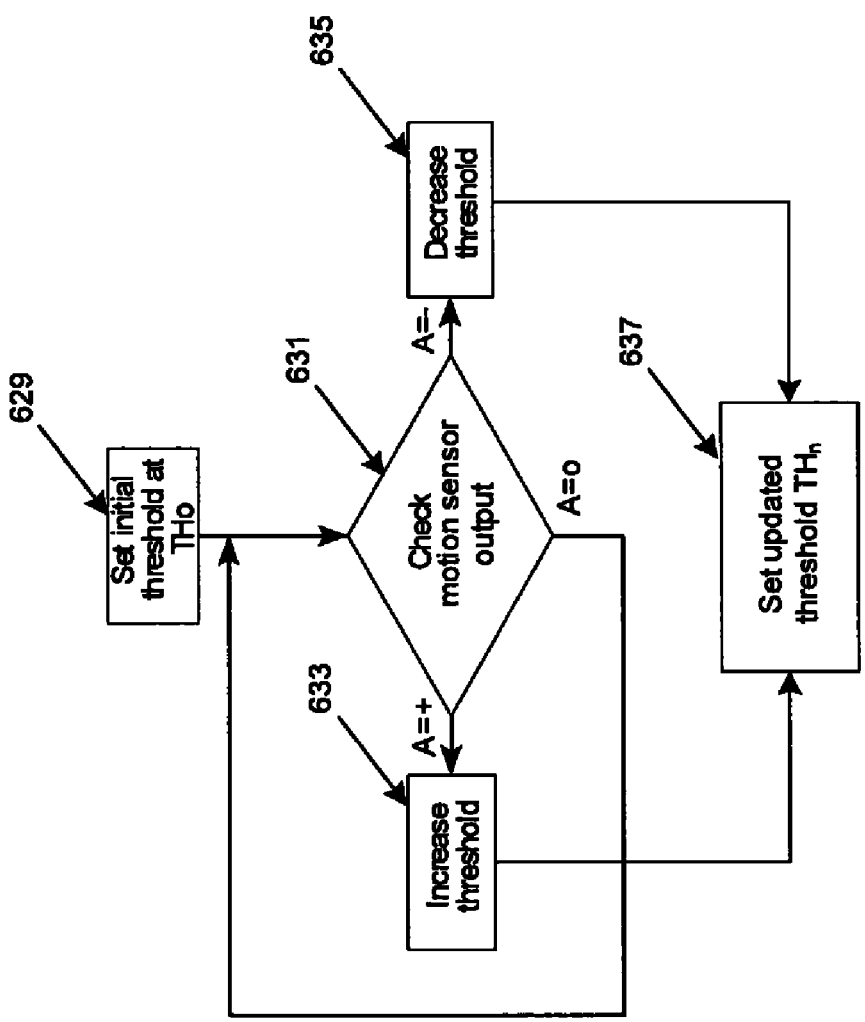
FIG. 6 shows a process flowchart providing steps for adjustment of a threshold value using a motion sensor.

FIG. 6 shows a process flowchart for adjusting the threshold value according to the signal indicative of motion. As mentioned above in relation to step 525 of FIG. 5, the signal indicative of motion is used to adjust the threshold value for the signal indicative of electrical activity of the heart. FIG. 6 illustrates the adjusting process in more detail.

The process illustrated in FIG. 6 begins with setting an initial threshold value $TH_0$ at step 629. The initial threshold value is programmable or may be a function of the average heart rate for a particular subject. The initial threshold value $TH_0$ is stored, for example, in memory 818.

A signal indicative of motion due to respiration is received at step 631. If the signal indicative of motion indicates an upward movement of the chest (e.g., "A=+" in FIG. 6), the threshold value will be increased as shown in step 633 and a new threshold value $TH_n^+$ will be stored at step 637. If the signal indicative of motion indicates a downward movement of the chest (e.g., "A=−" in FIG. 6), the threshold value will be decreased as shown in step 635 and a new threshold value $TH_n^-$ will be stored at step 637. If the signal indicative of motion indicates no significant movement of the chest (e.g., "A=0" in FIG. 6), the threshold value will remain the same and not be adjusted. As shown in the process flowchart of FIG. 6, the threshold value is adjusted according to the dynamic output of the signal indicative of motion to provide accurate heart rate detection. This updating can be continuous or periodic. The updated threshold value is stored in memory 818 and replaces the initial and previously stored values.

Figure 7:
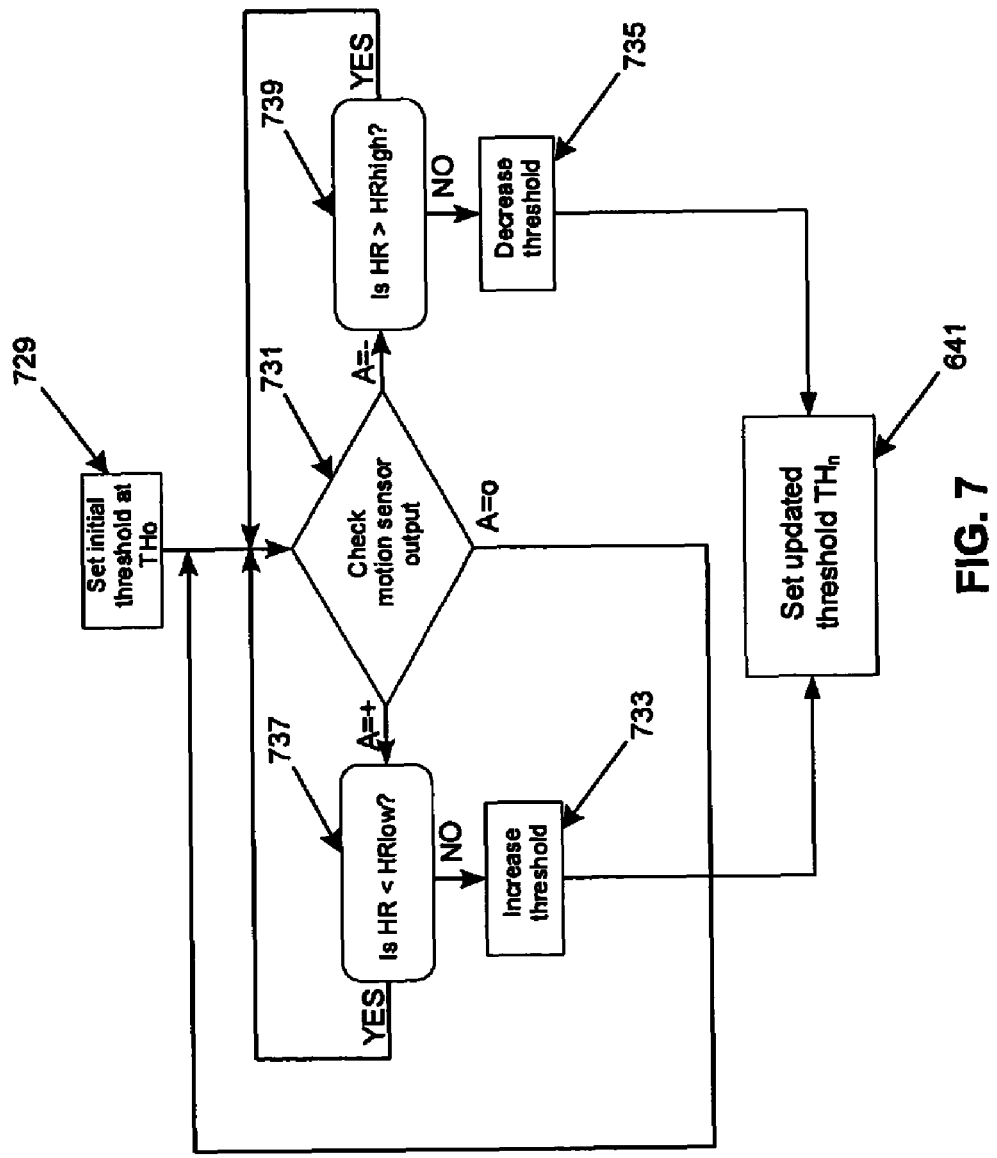
FIG. 7 shows a process flowchart providing steps for adjustment of a threshold value using a motion sensor including a check of the heart rate.

FIG. 7 illustrates another embodiment incorporating a check of the heart rate. More specifically, FIG. 7 shows a process flowchart for adjusting the threshold value according to the signal indicative of motion including a check of the heart rate to ensure that the threshold remains within an acceptable range. The acceptable range is defined by predetermined minimum and maximum heart rate values, which are programmable or may be a function of the average heart rate for a particular subject.

As in the process illustrated in FIG. 6, the process illustrated in FIG. 7 begins with setting an initial threshold value $TH_0$ at step 729. The initial threshold value is programmable or may be a function of the average heart rate for a particular subject. The initial threshold value may be stored, for example, in memory 818.

A signal indicative of motion due to respiration is received at step 731. If the signal indicative of motion indicates an upward movement of the chest (e.g., "A=+" in FIG. 7), the detected heart rate is compared with a predetermined minimum heart rate in step 737. If the detected heart rate is lower than the predetermined minimum heart rate, the threshold value could be set too high such that heart beats are not being detected. In this case, the threshold value is not increased regardless of the signal indicative of motion until the detected heart rate reaches an acceptable level. Thus, if the detected heart rate is lower than the predetermined minimum heart rate, the threshold value remains the same and is not adjusted. If the detected heart rate is higher than the predetermined minimum rate and therefore within the acceptable range, the threshold value will be increased as shown in step 733 and a new threshold $TH_n^+$ is set at step 741.

If the signal indicative of motion indicates a downward movement of the chest (e.g., "A=−" in FIG. 7), the detected heart rate is compared with a predetermined maximum heart rate in step 739. If the detected heart rate is higher than the predetermined maximum heart rate, the threshold value could be set too low such that baseline noise is being detected as heart beats. In this case, the threshold value should not be decreased regardless of the signal indicative of motion until the detected heart rate reaches an acceptable level. Thus, if the detected heart rate is higher than the predetermined minimum heart rate, the threshold value remains the same and is not adjusted. If the detected heart rate is lower than the predetermined maximum rate and therefore within the acceptable range, the threshold value will be decreased as shown in step 735 and a new threshold $TH_n^-$ is set at step 741.

If the signal indicative of motion indicates no movement of the chest (e.g., "A=0" in FIG. 7), the threshold value will remain the same and not be adjusted. As illustrated in the process flowchart of FIG. 7, the process includes a check of the heart rate before adjusting the threshold value to ensure that the threshold value remains within an acceptable range. The threshold value is dynamically adjusted according to the output of the signal indicative of motion to provide accurate heart rate detection. The adjusted threshold value may be stored, for example, in memory 818 and replaces the initial and previously stored threshold values.

The present invention is described in the environment of an external heart rate monitor. In such an external implementation, the motion signal can be generated, for example, by an external accelerometer or strain gauge-type sensor placed externally on the chest or abdominal surface of a patient. Alternatively, when a patient's breathing is being controlled by a ventilator, a signal representative of inhalation and/or exhalation can be generated by the ventilator and provided to the external heart rate monitor for use in detection threshold adjustment. The source of the motion signal is not critical. What is important is the ability to adjust the threshold of the heart rate monitoring signal to obtain accurate heart rate monitoring when the patient's chest is moving.

CONCLUSION

Example embodiments of the methods, systems, and components of the present invention have been described herein. As noted elsewhere, these example embodiments have been described for illustrative purposes only, and are not limiting. Other embodiments are possible and are covered by the invention. The present invention can be applied to detection of any signal in presence of any type of motion, as long as the effect of the motion on the sensor is known (e.g. it is known that an upward movement causes an increase in baseline or amplitude). Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. A method for detecting a heart rate of a patient, comprising the steps of:
    (a) sensing via a first sensor a first signal indicative of heart rate;
    (b) sensing via a second sensor a second signal indicative of motion of the patient's chest due to respiration;
    (c) adjusting a threshold value of the amplitude of the first signal based on the second signal; and
    (d) determining the heart rate as a function of the adjusted threshold value and the first signal,
    wherein step (c) comprises:
        increasing the threshold value in response to a determination of inflation of a patient's chest due to respiration,
        decreasing the threshold value in response to a determination of deflation of the patient's chest due to respiration, and
        keeping the threshold value constant in response to a determination of no substantial movement of the patient's chest.

2. The method of claim 1, wherein step (a) comprises sensing an electrocardiogram (ECG) signal.

3. The method of claim 2, wherein step (a) comprises sensing the ECG signal from subcutaneous electrodes placed in a chest area.

4. The method of claim 2, wherein step (a) comprises sensing the ECG signal from surface electrodes placed on a chest area of the patient.

5. The method of claim 1, wherein step (b) comprises sensing the second signal via a motion sensor.

6. The method of claim 5, further comprising locating the motion sensor on a surface of the patient's body.

7. The method of claim 1, wherein step (c) further comprises:
    comparing the adjusted threshold value with a predetermined maximum value; and
    keeping the threshold value constant if the adjusted threshold value would be above the predetermined maximum heart rate value.

8. The method of claim 1, wherein step (c) further comprises:
    comparing the adjusted threshold value with a predetermined minimum value; and
    keeping the threshold value constant if the adjusted threshold value would be below the predetermined minimum value.

9. The method of claim 1, wherein step (a) comprises sensing a photoplethysmography (PPG) signal.

10. A system for detecting a heart rate of a patient, comprising:
    first sensing means for sensing a first signal indicative of heart rate;
    second sensing means for sensing a second signal indicative of motion of the patient's chest due to respiration;
    means for adjusting a threshold value of the amplitude of the first signal based on the second signal; and
    means for determining the heart rate as a function of the adjusted threshold value and the first signal,
    wherein the means for adjusting a threshold value is configured to increase the threshold value in response to a determination of inflation of the patient's chest due to respiration, decrease the threshold value in response to a determination of deflation of the patient's chest due to respiration, and to not change the threshold value in response to a determination of no substantial movement of the patient's chest.

11. The system of claim 10, wherein the first signal is an electrocardiogram (ECG) signal.

12. The system of claim 11, wherein the ECG signal is produced from a plurality of subcutaneous electrodes configured to be placed in a chest area of the patient.

13. The system of claim 11, wherein the ECG signal is produced from a plurality of surface electrodes configured to be placed on a chest area of the patient.

14. The system of claim 10, wherein the second sensing means for sensing the second signal indicative of motion comprises a motion sensor.

15. The system of claim 14, wherein the motion sensor comprises at least one of an accelerometer, a velocity sensor, or a displacement sensor.

16. The system of claim 10, wherein the means for adjusting the threshold value is configured to keep the threshold value constant if the threshold value would be adjusted above a predetermined maximum value.

17. The system of claim 10, wherein the means for adjusting the threshold value is configured to keep the threshold value constant if the threshold value would be adjusted below a predetermined minimum value.

18. The system of claim 10, wherein the first signal is a photoplethysmography (PPG) signal.

19. An implantable cardiac device, comprising:
a physiologic sensor configured to produce a first signal indicative of heart rate;
a motion sensor independent of the physiologic sensor and configured to produce a second signal indicative of motion of a patient's chest due to respiration; and
a processor configured to:
adjust a threshold value of the amplitude of the first signal based on the second signal; and
determine the heart rate as a function of the adjusted threshold value and the first signal,
wherein the processor is configured to increase the threshold value upon a determination of an inflation of a subject's chest due to respiration, the processor is configured to decrease the threshold value upon a determination of a deflation of the subject's chest due to respiration, and the processor is configured to maintain the threshold value as substantially constant upon a determination of no substantial movement of the subject's chest.

20. The implantable cardiac device of claim 19, wherein the first signal is an electrocardiogram (ECG) signal.

21. The implantable cardiac device of claim 19, wherein the motion sensor comprises at least one of an accelerometer, a velocity sensor, or a displacement sensor.

22. A method for detecting a heart rate of a patient, comprising:
(a) sensing a first signal indicative of a heart rate of a patient's heart;
(b) sensing a second signal indicative of motion due to the patient's respiration, wherein the second signal is sensed independently of the first signal;
(c) as a function of the second signal, adjusting an amplitude threshold value associated with the first signal, said adjusted amplitude threshold value being indicative of an amplitude value that the first signal usually exceeds only during a contraction of the patient's heart; and
(d) detecting the heart rate based on a comparison of the first signal with the adjusted amplitude threshold value, wherein step (c) comprises:
increasing the amplitude threshold value in response to a determination of inflation of a patient's chest due to respiration,
decreasing the amplitude threshold value in response to a determination of deflation of the patient's chest due to respiration, and
keeping the amplitude threshold value constant in response to a determination of no substantial movement of the patient's chest.

23. The method of claim 22, further comprising repeating steps (a) through (d) to dynamically adjust the amplitude threshold value over time.

24. A system for detecting a heart rate of a patient, comprising:
first means for sensing a first signal indicative of a heart rate of a patient's heart;
second means for sensing a second signal indicative of motion due to the patient's respiration, wherein the second means is independent of the first means and the second signal is thereby independent of the first signal;
means for adjusting an amplitude threshold value associated with the first signal and configured to adjust said amplitude threshold value as a function of the second signal, wherein said adjusted amplitude threshold value is indicative of an amplitude value that the first signal usually exceeds only during a contraction of the patient's heart; and
means for detecting the heart rate based on a comparison of the first signal with the adjusted amplitude threshold value,
wherein the means for adjusting an amplitude threshold value is configured to increase the amplitude threshold value in response to a determination of inflation of the patient's chest due to respiration, decrease the amplitude threshold value in response to a determination of deflation of the patient's chest due to respiration, and to not change the amplitude threshold value in response to a determination of no substantial movement of the patient's chest.

25. The system of claim 24, wherein:
the first means comprises means for dynamically sensing the first signal over time;
the second means comprises means for dynamically sensing the second signal over time;
the means for adjusting the amplitude threshold value comprises means for dynamically adjusting the amplitude threshold value over time; and
the means for detecting the heart rate comprises means for dynamically detecting the heart rate based on repeated comparisons over time.

26. An implantable cardiac device (ICD), comprising:
a physiologic sensor configured to produce a first signal indicative of a heart rate of a patient's heart;
a motion sensor independent of the physiologic sensor and configured to produce a second signal indicative of motion due to the patient's respiration, whereby the second signal is independent of the first signal; and
a processor configured to:
adjust an amplitude threshold value associated with the first signal, said adjustment being a function of the second signal;
adjust said amplitude threshold value such that said adjusted threshold value is indicative of an amplitude value that the first signal usually exceeds only during a contraction of the patient's heart; and
detect the heart rate based on a comparison of the first signal with the adjusted amplitude threshold value.

27. The ICD of claim 26, wherein:
said physiologic sensor and said motion sensor are configured to produce the first signal and the second signal over a period of time spanning a plurality of respiratory cycles of the patient; and said processor is configured to adjust the amplitude threshold dynamically over time in response to the first signal and the second signal produced over the period of time.

28. The ICD of claim 26, wherein the processor is configured to increase the amplitude threshold value upon a determination of an inflation of a subject's chest due to respiration, the processor is configured to decrease the amplitude threshold value upon a determination of a deflation of the subject's chest due to respiration, and the processor is configured to maintain the amplitude threshold value as substantially constant upon a determination of no substantial movement of the subject's chest.

* * * * *